United States Patent [19]

Berglund

[11] 4,416,657

[45] Nov. 22, 1983

[54] ABDOMINAL CATHETER IMPLANT

[76] Inventor: Rickey T. Berglund, 2275-68 Caminito Pescado, San Diego, Calif. 92107

[21] Appl. No.: 407,744

[22] Filed: Aug. 13, 1982

[51] Int. Cl.³ .............................................. A61M 25/00
[52] U.S. Cl. ......................................... 604/9; 604/29; 604/33; 604/175
[58] Field of Search .................... 604/8, 9, 29, 28, 33, 604/175, 283, 264

[56] References Cited

U.S. PATENT DOCUMENTS

| | | | |
|---|---|---|---|
| 3,540,451 | 11/1970 | Zeman | 604/8 X |
| 3,995,642 | 12/1976 | Adair | 604/8 |
| 4,190,047 | 2/1980 | Jacobsen et al. | 604/28 |
| 4,239,041 | 12/1980 | Popovich et al. | 604/29 |
| 4,256,102 | 3/1981 | Monaco | 604/8 |
| 4,375,816 | 3/1983 | Lobianca | 604/8 |

*Primary Examiner*—Stephen C. Pellegrino
*Attorney, Agent, or Firm*—Gordon L. Peterson

[57] ABSTRACT

A catheter implantable in a living subject for supplying fluid to a first chamber in the body of the subject and allowing fluid to pass from the first chamber into a second chamber of the subject through a valve arrangement operable from the exterior of the subject. An operating device functions in conjunction with the implanted catheter to supply fluid to the first chamber, and to operate the valve arrangement.

17 Claims, 7 Drawing Figures

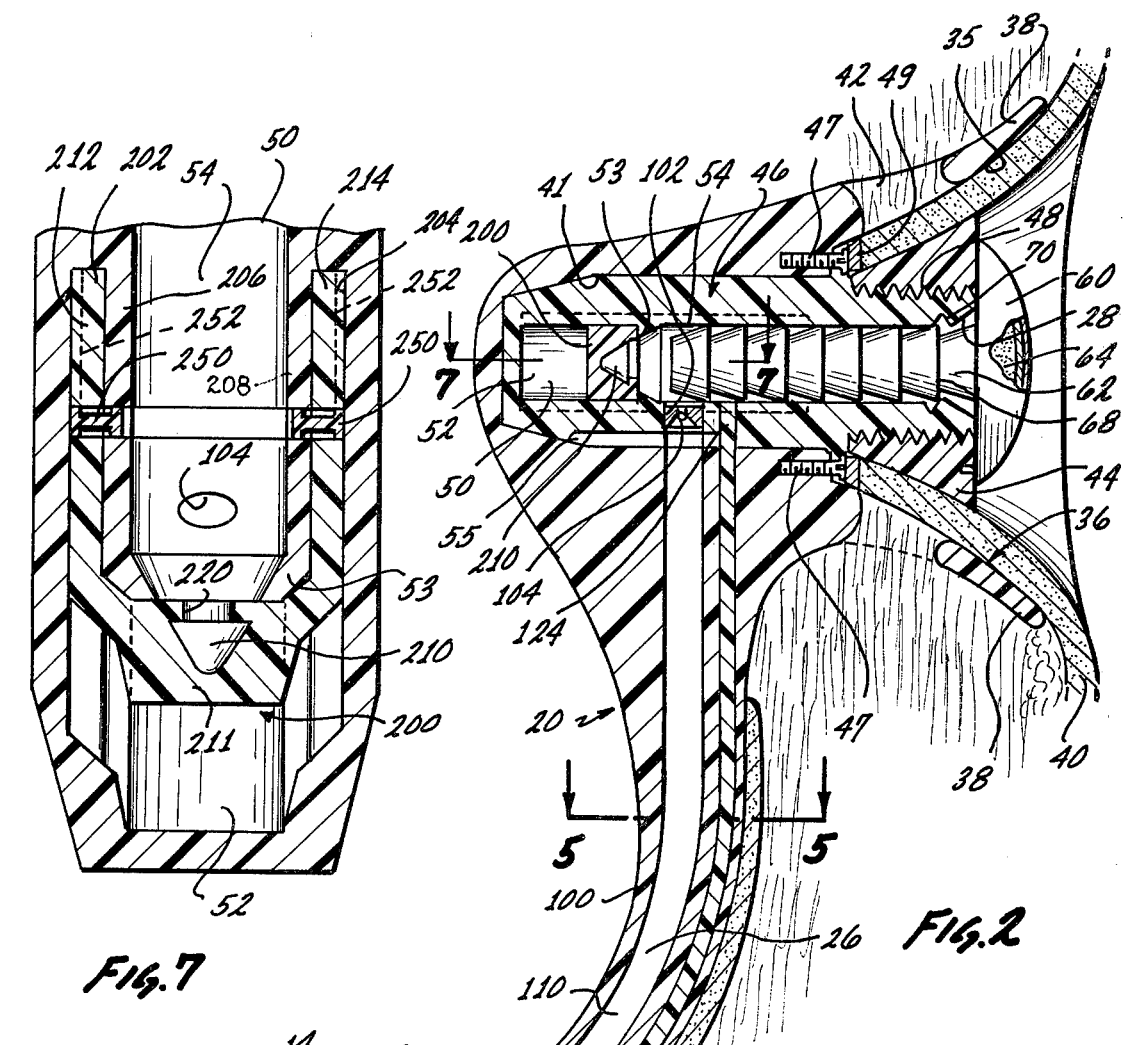

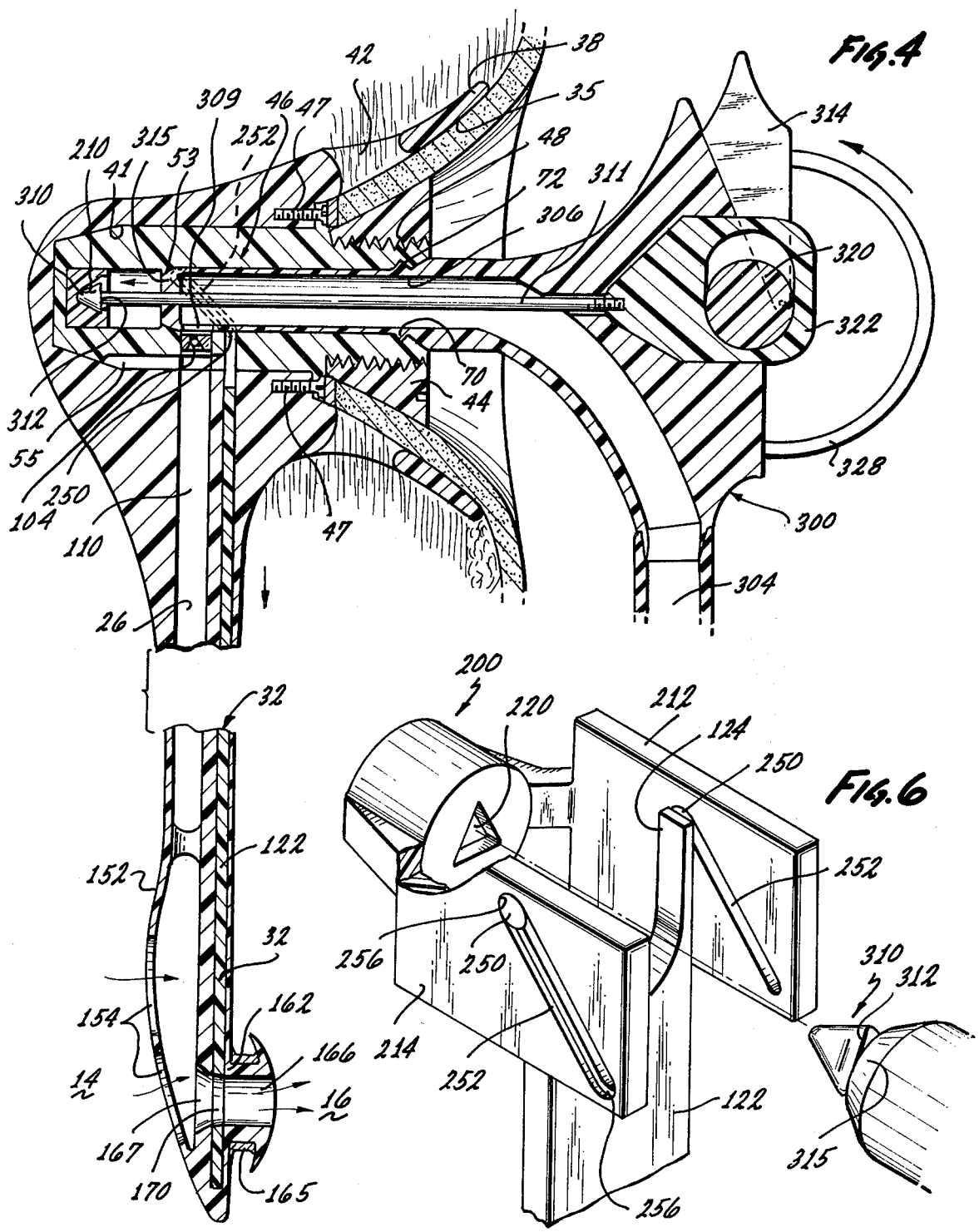

ABDOMINAL CATHETER IMPLANT

BACKGROUND OF THE INVENTION

The present device relates generally to medical implant devices for use in living subjects for supplying fluid to a particular body chamber of the subject.

Generally speaking, in procedures such as peritonal dialysis treatment, a dialysis fluid is introduced into the peritoneal cavity of a subject. The fluid is allowed to remain in the peritoneal cavity for a length of time and is then withdrawn. This type of dialysis or detoxifying treatment substitutes for the function of the kidneys to excrete metabolic waste products from the body of the subject and helps to regulate fluid electrolyte and acid-base balance in the body. At times, a catheter is implanted in the body of the subject, and repeated access to the peritoneal cavity is possible from outside of the body of the subject through the catheter.

In the prior art, the use of an implantable catheter to transfer fluid to a cavity of a subject, such as the peritoneal cavity, is well known. For example, U.S. Pat. No. 4,256,102 to Monaco shows a method and means of peritoneal dialysis in which a dialyzing tube is permanently embedded in a subject's body. To perform the dialysis treatment, the epidermis of the subject is pierced with a needle and a dialyzing fluid is introduced through the needle into the dialyzing tube and therethrough to the peritoneal cavity of the subject. The dialyzing fluid, after its dwell time in the peritoneal cavity, contains contaminants and is removed by being siphoned out and/or by gravity action. it can be seen that this device requires repeated puncturing of the epidermis of the subject. The punctured epidermis requires time to heal and presents a great discomfort to the subject.

U.S. Pat. No. 4,239,041 to Popovich et al. discusses a method of peritoneal dialysis used with a balloon catheter implanted in a subject and an external quick-connect coupling attached to the catheter. The dialysis fluid infusion system and the drainage system communicate through the quick-connect coupling with the peritoneal cavity. The quick-connect coupling extends through the abdominal wall of the subject and remains exposed. This arrangement leaves an unsightly tube protruding from the body of the subject and may be prone to infection.

In U.S. Pat. No. 4,190,047 to Jacobsen et al., an implanted peritoneal dialysis catheter is shown. It is stated as extending into the peritoneum and having an enlarged portion under the skin of the subject. When peritoneal dialysis is to be accomplished, the catheter is accessed by a cannula inserted through the abdomen of the subject. The dialysis fluid is supplied and removed through the cannula. The cannula obtains access to the implanted catheter through the abdominal wall.

It can be seen from the above patents that in cases where an implanted catheter to provide access to a cavity in the body of a subject is utilized, communication through the catheter is obtained either by a coupling which protrudes outside the abdomen of the subject or through a puncture made in the epidermis. The exposed portion of the catheter makes it vulnerable to environmental hazards and makes the subject susceptible to infection.

In the implanted catheter described in the above patent, the catheter is utilized to supply dialysis fluid to a cavity in the body of the subject as well as to remove the dialysis fluid after it serves its purpose. In such cases, obstruction and/or slow withdrawal of the dialysis fluid may occur due to the small diameter of the catheter tube, possible clotting, and the upward ascent of the dialysis solution during withdrawal against the gravitational force.

Further, in the prior art implantable catheter, if the catheter malfunctions after implantation, it is necessary to completely remove the malfunctioning catheter and replace it. With the prior art, removal of the malfunctioning catheter may require surgery.

SUMMARY OF THE INVENTION

The disadvantages and limitations of the prior art are overcome by the present invention. With this invention, an implanted catheter is used to pass dialysis fluid into the peritoneal cavity of the subject. After a dwell time, the dialysis fluid is passed from the peritoneal cavity into the bladder of the patient where it can be removed by urination. Accordingly, the removal process is carried out naturally. The catheter preferably includes a valve for controlling the passage of the dialysis fluid from the peritoneal cavity to the bladder. The valve can be remotely operated.

The catheter of this invention is particularly adapted for allowing dialysis fluid to be introduced into the peritoneal cavity and controlling the flow of that fluid to the bladder. However, in a broader sense, the catheter of this invention is also applicable to introducing fluid into a first chamber in the body of a subject and controlling the passage of fluid from the first chamber into a second chamber. For example, if the first chamber is the peritoneal cavity the second chamber may be in any elimination tract such as the intestines or the urinary tract. Although the catheter is particularly adapted for use with humans, it can also be used with animals.

Generally, the catheter comprises a body and certain movable components within the body. With this invention, the movable components can be removed from the body for inspection, cleaning, repair, etc. Thus, surgery is unnecessary for carrying out these functions on the removable components of the catheter. The body and nonremovable components of the catheter are much less likely to require inspection, repair or replacement.

The present invention provides an implantable catheter having a body adapted for implantation in a subject and having a proximal end and a distal end; means for mounting said body of the catheter in the subject with the proximal end adjacent to the exterior of the subject and with the body of the catheter extending into the interior of the subject. The body is provided with passage means leading from a location adjacent the proximal end to substantially the distal end of the catheter. The passage means serves as a passage for fluid. The passage means has an inlet means adjacent the proximal end and an outlet means communicating with the first chamber when the catheter is implanted in the subject, whereby a fluid can be passed from the inlet means through the passage means and the outlet means to the first chamber. The body of the catheter is further provided with a valve means for controlling the flow of the fluid therethrough from the first chamber to the second chamber. The valve means is operable from exterior of the body of the subject.

BRIEF DESCRIPTION OF THE DRAWINGS

FIG. 2 is a detailed sectional view of the catheter implanted in a subject;

FIG. 4 is a sectional view of the catheter and catheter operating means with the operating means in a second position to cause the valve means of the catheter to operate to permit removal of fluid supplied to the first chamber. For simplicity, the catheter is not shown in its curved implanted condition of FIG. 1.

FIG. 5 is a sectional view taken along 5—5 of FIG. 2, showing the fluid passage means and the flexible band.

FIG. 6 is a perspective view, partly in section, of the piston, its lateral arms, the flexible band of the catheter of FIG. 2, and the head of the operating means.

FIG. 7 is a fragmentary sectional view taken along line 7—7 of FIG. 2 of the piston in its first position, the first and second compartments, and pins connecting the lateral arms to the flexible band.

DETAILED DESCRIPTION OF THE PREFERRED EMBODIMENT

Figure 1:
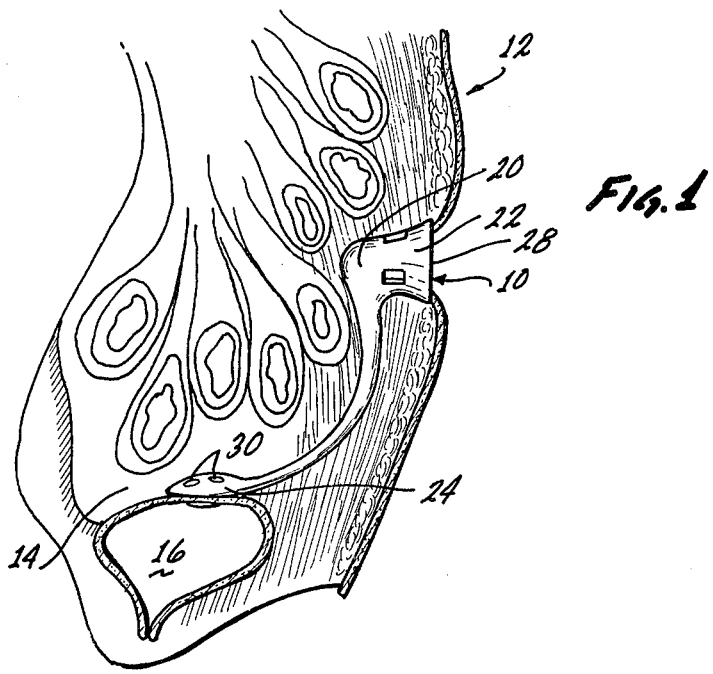
FIG. 1 is a cross-sectional view of the catheter of the present invention implanted in a human.

FIG. 1 shows an implantable catheter 10 implanted in a body 12 of a patient or subject. The subject has a first chamber 14 in the form of a peritoneal cavity and a second chamber 16 in the form of a bladder 16.

The catheter 10 comprises a body 20 having a proximal 22 and a distal end 24. The body 20 of the catheter is implanted in the subject with the proximal end 22 mounted adjacent the exterior of the subject. A fluid passage means 26 (FIGS. 2 and 4) is provided in the body 20 and leads from a location adjacent the proximal end to substantially the distal end 24 of the body 20. The passage means 26 has an inlet means 28 adjacent the proximal end 22 and an outlet means 30 communicating with the peritoneal cavity 14 when the catheter is implanted in the subject. With this arrangement, a fluid can be passed from the exterior of the subject 10 to the inlet means 28, and through the passage means 26 and the outlet means 30 to the bladder 16. Valve means 32 (FIGS. 2 and 4) is provided for controlling the flow of the fluid therethrough from the cavity 14 to the bladder 16. The valve means 32 is operable from the exterior of the body or subject 12.

In the catheter of FIG. 1, fluid such as dialysis fluid, is introduced through the inlet means 28. The fluid passes through the passage means 26 into the outlet means 30 and therethrough into the peritoneal cavity 14. The fluid remains in the cavity 14 for a certain dwell time and functions to extract certain toxic materials therefrom. The valve means 32 is then operated from exterior of the subject 12 to cause the dialysis fluid to be passed into the bladder 16 under the force of gravity and the pressure of the fluid in the peritoneal cavity 14 where it can be eliminated by urination. The valve means 32 is closed after the fluid supplied to the cavity 14 has passed into the bladder 16. A fresh sample of an appropriate fluid may be introduced into the cavity 14 after the valve means 32 has been closed to replenish the natural body fluids that were present in the peritoneal cavity 14 and which may have passed into the bladder along with the supplied fluid.

In FIG. 1, at least two important aspects of the present invention can be noted. One aspect is the contour and configuration of the catheter which permits its implantation in a very convenient manner in the subject. Another important aspect is the provision of the valve means which permits the fluid supplied to a first chamber to be passed to a second chamber within the subject.

The body 20 at the proximal end 22 comprises a frusto-conical bowl member 36 (FIG. 2) formed by a plurality of flared strut elements 38. The frusto-conical bowl underlies an opening in the patient's skin 40 and has ingrowth ports 42 which contribute to the sealing of the patient's skin 40 into and around the frusto-conical bowl member 36. The patient's skin 40 is captured between the inner surface 35 of the bowl member 36 and a wedging seal 44, as shown. The wedging seal 44 holds the skin 40 in a snug contact with the surface 35, thereby facilitating the ingrowth of the skin in the ingrowth ports 42. A detailed description of the frusto-conical bowl member 36 and the ingrowth ports 42 can be obtained from my application for IMPLANTABLE DEVICE FOR INTRAVASCULAR ACCESS, Ser. No. 342,113 filed Jan. 25, 1982, the disclosure of which is hereby incorporated by reference into the present application.

The body 20 has chamber means 41 in which a capsule or capsule means 46 is received. The capsule means 46 has a threaded outer end 48 and the wedging seal 44 is screwed onto the outer end 48. It can be seen that when the wedging seal 44 is screwed onto the outer end 48 of the capsule, it captures and holds the skin 40 between its outer surface and the inner surface 35 of the bowl member 36. The capsule 46 is removably secured to the bowl member 36 by attaching means 47, shown as screws in FIGS. 2, 3 and 4. An appropriate overlay 49 covers the attaching means 47. The overlay 49 is an ingrowth base, made of a material such as pyrolitic carbon, to which living tissues are capable of bonding.

The capsule 46 has a longitudinal axial bore 50 therein. A plug 60 is provided for sealing the outer or exterior opening of the axial bore 50. The plug 60, which is formed of a somewhat resilient, biologically compatible plastic, comprises a somewhat expandable shaft 62 and a domed head 64. The shaft 62 may be expanded through use of a salt solution injected through a self-sealing port in the domed head 64. Serrations 68 on the shaft 62 assure a snug contact between the plug in the axial bore. The salt solution in the shaft saturates the bore to prevent invasion by bacteria. The plug 60 is an anti-bacterial seal.

The shaft 62 and the domed head 64 are preferably made in a flesh-toned color so as to minimize their visibility. Preferably, the domed head 64 is situated to simulate the navel of the patient and the catheter 10 is implanted with the bore 50 positioned at the navel. In this case, the skin 40 shown in FIG. 2 to be captured between the conical wedging seal 44 and the bowl member 36, would represent the skin surrounding the navel of the patient. In this manner the proximal end of the catheter 10 is cosmetically attached behind the navel and the natural indentation of the navel provides a generally unobtrusive site for the catheter.

A helical groove 70 is provided at the outer end of the bore 50. The groove 70 receives a complementary thread 72 of an activation or operating device that fits in the bore 50, as shown in FIG. 4 and described hereinbelow. The serrations 68 are configured to make it easy to insert the plug 60 into the bore 50.

The axial bore 50 in the capsule comprises a first compartment 52 and a second compartment 54 separated by a shoulder 53, as shown in FIG. 2 and in FIG. 7. The first compartment 52 has side channels 202 and 204 extending parallel to a portion of the second compartment 54, and separated therefrom by walls 206 and 208. The shoulder 53 is formed at one end of the walls 206 and 208.

A piston 200 is movably situated in the bore 50 which is configured to allow movement of the piston 200 therein. The piston 200 has a nose 211 and integral lateral arms 212 and 214, (FIGS. 6 and 7) which are slidably received in channels 202 and 204, respectively. The piston 200 is prevented from moving into the second compartment 54 by the shoulder 53.

Figure 3:
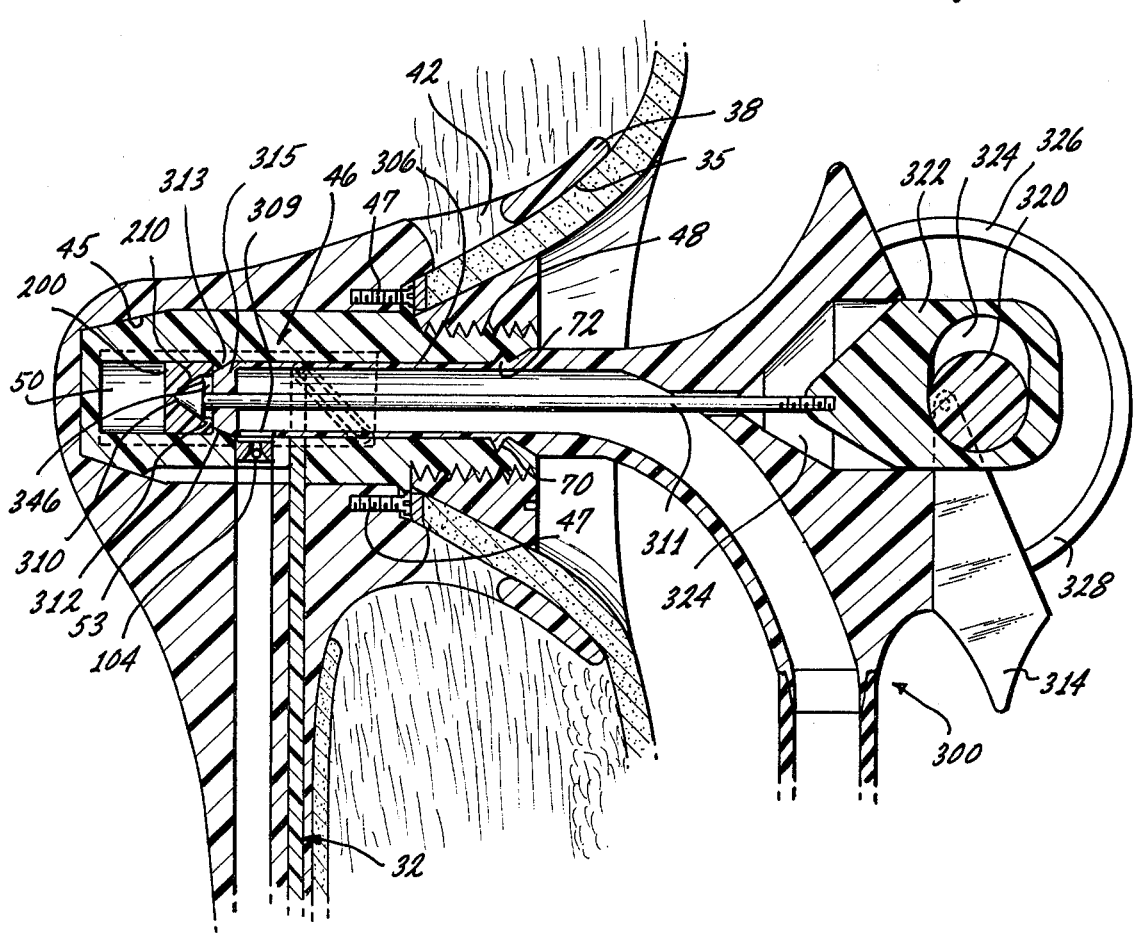
FIG. 3 is a sectional elevational view of the catheter operating means and a proximal portion of the catheter in an initial position to supply fluid to the catheter and therethrough to a first chamber of the subject.

The piston 200 has a recess 210 provided in the nose 211. The recess 210 has somewhat conical interior and a triangular opening 220 to receive a head 310 therein of an activating device 300. The recess 210 is shown in FIGS. 2, 3, 4 and 7, and the head 310 is shown in FIGS. 3 and 6. In FIG. 4, the head 310 is shown positioned in the recess 210. Immediately past the opening 220, the recess 210 is enlarged to accommodate the head 310 passing through the opening 220. The head 310 is adapted to pass through the opening 220 and to be turned slightly, whereby a trailing triangular edge 312 thereof is captured in the enlarged space. In this manner, the head 310 is securely retained within the piston 200. It will be apparent that a different means of securing the piston 200 to the head 310 could be utilized.

The capsule 46 has a channel 55 therein, as shown in FIGS. 2 and 4. This channel 55 will be utilized when the capsule 46 is removed, and the function thereof, as described more fully hereinbelow, is to accommodate a sliding band 122 which is attached to the capsule 46. In brief, the channel 55 is configured such that the sliding band 122 and the capsule 46 can both occupy the space of chamber means 41 as the capsule 46 is being removed.

Looking now to FIG. 7, the capsule 46 has an opening 102 with a check valve 104 therein as shown in FIGS. 2 and 4. This opening 102 leads to the passage means 26.

Looking at FIGS. 2, 4 and 5, body 20 has an elongated connecting portion 100, passage means 110 which forms part of the passage means 26 and a canal 120. The passage means 110 is adapted to allow fluid to flow therethrough. The canal 120 receives the sliding flexible band 122, and permits a sliding movement thereof. The flexible band 122 is part of valve means 32, which controls the flow of fluid from the cavity 14 to the bladder 16 (FIG. 1). The passage means 110 communicates with the second compartment 54 at its upper end 113 through the valve 104 (FIG. 2). Similarly, the canal 120 communicates with the second compartment 54 at its outer or upper end 124. The passage means 110 may be generally elliptical in shape (FIG. 5) and the canal 120 may be in the shape of a segment of a circle. It is to be understood that the arrangement of the passage means 110 and the canal 120 is shown only as a representative sample, and not by way of any limitation of the present invention.

The distal end 24 is implanted in the peritoneal cavity 14 and comprises of a domed housing 152 having a plurality of openings 154 which form the outlet 30 which communicates with the peritoneal cavity 14. The domed housing 152 forms a cover for an outlet chamber or reservoir that 156 receives fluid passed down through the passage means 110. The chamber 156 allows a central distribution of the fluid into the cavity 14. The catheter 10 is made from a material such that the domed housing maintains the integrity of its structure.

The valve means 32 comprises a seat 162 coupled to a wall 164 of the bladder 16 by an ingrowth ring 165 to which bladder tissue attaches and having an opening 166 which communicates with the bladder. There is a second opening 167 provided in the body 20 of the catheter, which communicates with the cavity 14. The fluid path between the cavity 14 and the bladder 16 may be blocked by a portion 168 of the sliding band 122, in the first position of the sliding band. The flexible band 122 has an opening 170 which in a second position of the flexible band 122 is aligned with the openings 166 and 167 to permit fluid communication between the cavity 14 and the bladder 16 through the chamber 156. The domed housing 152 inhibits blockage of the flow path between the cavity 14 and the bladder 16.

The flexible band 122 is coupled at its upper end to the lateral arms 212 and 214 of the piston 20 as shown in FIGS. 6 and 7 by means of pins 250. The lateral arms 212, 214 have inclined slots or grooves 252, which in the form shown, slope at about a 45° angle to the flexible band 122. The pins can translate within the slots 252. More specifically, the outer end of the sliding band 122 is generally a U-shape with parallel legs 124 of the U, attached respectively to lateral arms 212 and 214 through the pins 250.

Each of the slots 252 has a top end 254 and a lower end 256. When the pin 250 is situated at the top end 254, the sliding band 122 is elevated and the opening 170 in the sliding band is not aligned with the openings 166 and 167 as shown in FIG. 2. When the pins 250 are at the lower ends 256 of the slots 252, the opening 170 in the flexible band is disaligned with the openings 166 and 167 as shown in FIG. 4.

The activation device 300 comprises a tube 306 connected to a dialysis fluid source by conduit 304. The fluid source provides in measured quantity the particular fluid that is to be supplied to the cavity 14. The activation device 300 further comprises the head portion 310, a shaft 311, and a rotatable operating lever 314. The lever 314 is coupled to the shaft 312 through a rotatable eccentric or a cam 320 and a sliding block 322. The cam 320 is received within a cavity 324 provided in the sliding block 322. Angular movement of the lever 314 rotates the cam 320 to move the sliding block 322 axially within a bore 324 provided in the body of the activation device 300 as shown in FIGS. 3 and 4. A housing cover 326 is provided over the sliding block 322, and the housing cover has a slot 328 for movement of the lever 314 therein.

The sliding block 322 is connected at one end to the shaft means 312 whereby movement of the sliding member 322 causes movement of the shaft 311.

The shaft 311 extends through the tube 306 and through a fluid-tight opening 313 provided at the outer end of 315 of the tube. The outer end 315 of the tube 306 is configured to match and rest against the shoulder 53, as shown in FIGS. 3 and 4. Thus the shoulder 53 of the capsule 46 acts as a stop for the tube 306. The tube 306 is provided with an opening 309 which is aligned with the check valve 104 when the tube 306 is in its operative position within the bore 50.

As explained above, the head 310 is configured to complement the configuration of the recess 210 provided in the piston 200 and the trailing end 312 of the head generally conforms to the shape of the opening 220 to the recess 210 as shown in FIG. 6.

As described above, the catheter 10 is mounted at the proximal end 22 to the skin 40 and adjacent tissue around the navel and at the distal end 24 by the attachment of the seat 162 to the wall 164 of the bladder 16. The catheter 10 is initially in the generally curved condition shown in FIG. 2; however, it is sufficiently flexible, particularly along the connecting portion 100, to conform to various different anatomical shapes and to bend and flex during use. Except when the catheter 10 is being used to supply a dialysis fluid to the peritoneal cavity 14 or to drain the fluid from the cavity 14 to the bladder 16, the plug 60 is in position as shown in FIG. 2 to completely close and seal the bore 50 and hence the entrance to the passage means 26 leading to the peritoneal cavity.

In use, the plug 60 is manually withdrawn from the bore 50. With the piston 200 in the retracted position of FIG. 2, the sliding band 122 is in its upper position as shown in FIG. 7 to block communication between the peritoneal cavity 14 and the bladder 16. The piston 200 is held in the retracted position by friction of the arms 212 and 214 and the band 122 with the surfaces against which they slide and/or by a spring (not shown).

Next, the tube 306 is inserted into the bore 50 and the head 310 is inserted through the triangular opening 220 into the recess 210. The activating device is then rotated 180° to the position of FIGS. 3 and 4 to attach the device 300 to the capsule 46 with the groove 70 and the thread 72 and to angularly displace the head 310 relative to the triangular opening to lock the head in the recess 210.

With the components in this position, a dialysis fluid can be passed from a source (not shown) through the conduit 304, the tube 306, the opening 309, the check valve 104, the fluid passage means 110, and the openings 154 to the peritoneal cavity 14. The dialysis fluid is allowed to remain in the peritoneal cavity for a predetermined dwell time during which the fluid picks up body poisons. During this dwell time, the activation device 300 may be removed from the bore 50 of the catheter 10 and the plug 60 replaced.

At the conclusion of the dwell time, the activation device 300 is reinserted into the bore 50 as described above. The lever 314, which is suitably rotatably mounted on the body of the device 300, is then rotated from the position shown in FIG. 3 to the position shown in FIG. 4 to axially move the block 322, the shaft 311, the head 310 and the piston 200 to the left to the advanced position shown in FIG. 4. This causes the pins 250 to be driven downwardly in their respective slots 252 to thereby drive the sliding band 122 downwardly to the position of FIG. 4 in which the opening 170 in the band is aligned with the openings 166 and 167. This allows the fluid in the peritoneal cavity 14 to flow by gravity and/or contraction of the cavity 14 into the bladder 16 where such fluid can be eliminated by urination.

Rotation of the activation device 300 in attaching the threads 70 and 72 to mount the device on the capsule 46 angularly displaces the head 310 relative to the triangular opening 220. The head 310, in this embodiment, is generally in the shape of a triangular pyramid and the angular displacement is such that the head 310 cannot be removed from the recess 210. Accordingly, by returning the lever 314 from the position of FIG. 4 to the position of FIG. 3, and hence the head 310 to the position of FIG. 3, the head mechanically retracts the piston 200 to the position of FIG. 3. This raises the sliding band 122 to block communication between the peritoneal cavity 14 and the bladder 16.

Another important feature of this invention is that the parts which are more likely to require inspection, repair or replacement can be removed from the catheter 10 without surgery. To remove these components from the catheter 10, the seal 44 and the screws 47 are unscrewed, and this may require the severance of some of the skin and tissue adjacent these components. This permits the capsule 46 to be withdrawn with the piston 200 therein and with the band 122 attached to the piston. The channel 55 accommodates the band 122 and prevents the band from jamming against the periphery of the capsule 46 during the withdrawal movement. A new set of components can be inserted into the implanted catheter 10 by reversing the procedure described above while the removed set is being worked on. A number of factors such as gravity, bladder drainage, and muscular contraction of the cavity 14 can be used to prevent backflow from the bladder.

The catheter 10 must, of course, be constructed of suitable bio-compatible materials, such as suitable bio-compatible plastics. These materials, as well as the ingrowth materials to which body tissue is adapted to attach, are well-known by those having ordinary skill in the art.

Although an exemplary embodiment of the invention has been shown and described, many changes, modifications and substitutions may be made by one having ordinary skill in the art without necessarily departing from the spirit and scope of this invention.

I claim:

1. A catheter implantable in a living subject for supplying fluid to a first chamber in the body of the subject and controllably allowing fluid to pass from the first chamber into a second chamber of the subject, the catheter comprising:
   a body adapted for implantation in the subject and having a proximal end and a distal end;
   means for mounting said body in the subject with the proximal end adjacent to exterior of the subject and with the body extending into the interior of the subject;
   said body having passage means therein leading from a location adjacent the proximal end into the interior of the body;
   said passage means having inlet means adjacent said proximal end and outlet means communicating with said first chamber of the subject when the catheter is implanted in the subject whereby a fluid can be passed from the inlet means through the passage means and the outlet means to the first chamber; and
   valve means on the body for controlling the flow of the fluid therethrough from the first chamber to the second chamber.

2. The catheter of claim 1 wherein said valve means is operable from the exterior of the subject.

3. The catheter of claim 1 wherein said valve means comprises an elongated flexible band.

4. The catheter of claim 1 wherein said proximal end is adapted to be mounted at the navel of the subject.

5. The catheter of claim 1 wherein said mounting means includes means for mounting said distal end to said second chamber.

6. The catheter of claim 1 wherein said body comprises reservoir means at said distal end for collecting said fluid passed through the passage means and domed housing means covering said reservoir means, said domed housing having openings for allowing fluid collecting in said reservoir means to pass therethrough and into the first chamber.

7. The catheter of claim 1 wherein said body is bendable to generally conform to the anatomy adjacent the first and second chamber.

8. The catheter of claim 1 wherein said body comprises bowl means at said proximal end adapted to be implanted subcutaneously, said bowl means having chamber means therein and capsule means removably fitted in said chamber means and removable from the exterior of the subject, one-way valve means coupled to said capsule means for providing one-way access to said passage means.

9. The catheter of claim 8 wherein said capsule means comprises an axial bore means having first and second compartments, said second compartment adapted for receiving a plug therein and means for operating said valve means including piston means movably situated in said first compartment.

10. The catheter of claim 8 wherein said capsule means comprises axial bore means having first and second compartments, said second compartment adapted for receiving a plug therein, and piston means movably situated in said first compartment, said piston means having lateral arms movably retained in channel means provided in said capsule means, said lateral arms having groove means therein, pins means translatable in said groove means, said valve means comprising a flexible band coupled to said lateral arms through said pins, the translation of said pin in said groove means causing a sliding movement of said flexible band, said sliding movement causing said valve means to control the flow of fluid therein.

11. The catheter of claim 9 or 10 wherein said plug is expandible after being received in said second compartment.

12. The catheter of claim 8, further comprising a wedging seal, said bowl means being implanted subcutaneously with the skin of the subject being captured between the bowl means and said wedging seal.

13. The catheter of claim 1 wherein said body has a first opening means communicating with said first chamber and second opening means communicating with said second chamber; said valve means comprising an elongated flexible band interposed between said first chamber and said second chamber, said flexible band having a first position wherein fluid communication is prevented between said first and second chambers through said first and said second opening means through the valve means and a second position wherein fluid communication is provided between said first and second chambers through said first and second opening means.

14. A method of supplying fluid to a first chamber in the body of the subject and selectively allowing fluid to flow from the first chamber into a second chamber in the body of the subject comprising:
 a. supplying fluid through an implanted catheter into said first chamber;
 b. permitting said fluid to remain in said first chamber for a particular dwell time; and
 c. passing said fluid after said dwell time from said first chamber into said second chamber.

15. A method for carrying out peritoneal dialysis on a subject comprising the steps of:
 a. passing dialysis fluid through an implanted catheter into the peritoneal cavity of the subject;
 b. permitting said dialysis fluid to remain in said peritoneal cavity for a dwell time; and
 c. passing said dialysis fluid from the peritoneal cavity after said dwell time into an elimination tract of the subject for removal by a natural elimination process.

16. The method of claim 14 or 15 wherein the steps (a) through (c) are repeated a number of times.

17. The method of claim 15 wherein the last mentioned step of passing includes passing the dialysis fluid into the bladder for removal by urination.

* * * * *